United States Patent [19]

Ribi et al.

[11] Patent Number: 5,268,305

[45] Date of Patent: Dec. 7, 1993

[54] MULTI-OPTICAL DETECTION SYSTEM

[75] Inventors: Hans O. Ribi, San Mateo; Todd A. Guion; Joseph R. Murdoch, both of Burlingame; John C. Scott, Los Gatos; Victor Pan, Burlingame; Glenda L. Choate, Belmont, all of Calif.

[73] Assignee: Biocircuits Corporation, Sunnyvale, Calif.

[21] Appl. No.: 627,027

[22] Filed: Dec. 13, 1990

Related U.S. Application Data

[63] Continuation-in-part of Ser. No. 453,784, Dec. 20, 1989, abandoned, which is a continuation-in-part of Ser. No. 366,651, Jun. 15, 1989, Pat. No. 5,156,810.

[51] Int. Cl.[5] ............... G01N 33/53; G01N 21/01
[52] U.S. Cl. ............... 436/501; 436/164; 436/172; 436/527; 436/528; 436/531; 436/805; 422/681; 422/82.05; 422/82.08; 422/82.09; 435/291
[58] Field of Search ............... 436/501, 527, 528, 531, 436/805, 164, 172; 422/68.1, 82.05, 82.08, 82.09; 435/291

[56] References Cited

U.S. PATENT DOCUMENTS

| Re. 33,064 | 9/1989 | Carter et al. | 436/805 |
| Re. 33,581 | 4/1991 | Nicoli et al. | 422/82.05 |
| 4,054,646 | 10/1977 | Giaever | 436/805 |
| 4,299,916 | 11/1981 | Litman et al. | 436/805 |
| 4,521,522 | 6/1985 | Lundstrom et al. | 436/805 |
| 4,558,013 | 12/1985 | Murinkovich et al. | 422/82.09 |
| 4,621,063 | 11/1986 | Wyatt et al. | 436/805 |
| 4,661,442 | 4/1987 | Lukens | 436/528 |
| 4,743,560 | 5/1988 | Campbell et al. | 436/528 |
| 4,859,538 | 8/1989 | Ribi | 435/4 |

Primary Examiner—James C. Housel
Assistant Examiner—Jan M. Ludlow
Attorney, Agent, or Firm—Bertram I. Rowland

[57] ABSTRACT

Apparatus and methods are provided for the detection of analytes. A polyunsaturated polymerized lipid layer is employed, which is anisotropic, has a member of a specific binding pair bound to an end of the lipids, and whose optical characteristics are modified upon complex formation between the specific binding pair member and its complementary member. By providing for polarized light, linear and/or circular, one can detect the presence of complex formation by the change in the optical characteristics of the film. Polarizers, analyzers, and wave plates are employed for providing for a light signal which can be analyzed and related to the presence of an analyte in a sample.

5 Claims, 1 Drawing Sheet

MULTI-OPTICAL DETECTION SYSTEM

CROSS REFERENCE TO RELATED APPLICATIONS

This Application is a continuation-in-part of Application Ser. No. 07/453,784, filed Dec. 20, 1989 now abandoned; which is a continuation-in-part of Application Ser. No. 07/366,651, filed Jun. 15, 1989 now U.S. Pat. No. 5,156,810 which disclosures are incorporated herein by reference.

INTRODUCTION

1. Technical Field

The field of this invention is the detection of molecules by means of optically anisotropic materials capable of binding to a substance to form a specific binding pair.

2. Background

As the world has become more complex and as our understanding of different phenomena has increased, there has been a concomitant need to improve methods of measuring the wide variety of substances. From the clinical laboratory, there has been increasing interest in being able to measure various substances in the doctor's office, the home, at bedside, in the field, as well as other sites. With the continuously increasing number of physiologically active substances, both naturally occurring and synthetic, there has been a desire to be able to measure the substances as indicative of the health status of an individual, for therapeutic dosage monitoring, for research, and the like. The substances may be found in a wide variety of samples, ranging over numerous orders of magnitude in concentration for their dynamic ranges of activity, and further differ as to the ease with which one may detect their presence. An area which has only recently assumed substantial commercial importance and will be of increasing importance is the detection of specific nucleotide sequences. Nucleotide sequences find application in genetic counseling, forensic medicine, detection of diseases, and the like. There is, therefore, a wide diversity of opportunities to measure diverse substances from different sources with different sensitivities and for a wide range of purposes.

The methods for detection have ranged from radioactive labels, light absorption, fluorescence, chemiluminescence, agglutination, etc. Each of these methods has found application and has disadvantages as well as advantages over alternative methods. As yet, there has been no single method which has proven applicable in all situations. There is, therefore, substantial interest in devising new methods which may provide for significant opportunities in measuring compounds of interest, where the protocols, apparatus, or reagents may provide advantages over other techniques.

Relevant Literature

U.S. Pat. No. 4,489,133 describes procedures and compositions involving orderly arrays of protein molecules bound to surfactants. Thomas, et al., *Electron. Letters* (1984) 20:83-84 describe a GaAs/LB film MISS switching device employing ω-tricosenoic acid as the surfactant bilayer for producing a thin insulator. Lochner, et al., *Phys. Status Solidi* (1978) 88:653-661 describe photoconduction in polydiacetylene multilayer structures and single crystals. Sugi, *J. Molecular Electronics* (1985) 1:3-17 provides a review of Langmuir-Blodgett film use in electronics. Reynolds, ibid (1986) 2:1-21 describes conducting organic polymers. Wilson, *Electron. Letters* (1983) 19:237 describes the principles of a three dimensional molecular electronic memory employing polydiacetylene crystals or Langmuir-Blodgett multilayer films. Descriptions of electronic devices employing organized macromolecular ensembles formed with surfactant layer crystallization include Arrhenius, et al., *Proc. Natl. Acad. Sci. USA* (1986) 83:5355-5359; Haddon and Lamola, *Ibid* (1985) 82:1874-1878; and Paleos, *Chem. Soc. Rev.* (1985) 14:45-67. Vandevyer, et al., *J. Chem. Phys.* (1987) 87:6754-6763. U.S. Pat. No. 4,624,761. Fujiki, et al., *Amer. Chem. Society* (1988) 4:320-326. Biegajski, et al., *Amer. Chem Society* (1988) 4:689-693. Pecherz, et al., *Journal of Molecular Electronics* (1987) 3:129-133. Lando, et al., *Synthetic Metals* (1984) 9:317-327. Day, et al., *Journal of Applied Polymer Science* (1981) 26:1605-1612. Shutt, et al., *Amer. Chem. Society* (1987) 3:460-467. Dhindsa, et al., *Thin Solid Films* (1988) 165:L97-L100. Metzger, et al., *Amer. Chem. Society* (1988) 4:298-304. Fujiki, et al., *Amer. Chem. Society* (1988) 4:320-326. Wohltjen, et al., *IEEE Transactions on Electron Devices* (1985) 32:1170-1174. Wernet, et al., *Semiconducting L-B Films* (1984) 5:157-164. Sugi, et al., *Thin Solid Films* (1987) 152:305:326. Peterson, *Journal of Molecular Electronics* (1986) 2:95-99. Descriptions of methods for immobilizing biological macromolecules on polymerized surfactant films include: O'Shannessey, et al., *J. Appl. Bioch.* (1985) 7:347-355. Hashida, et al., *J. Appl. Biochem.* (1984) 6:56-63. Packard, et al., *Biochem.* (1986) 25:3548-3552. Laguzza, et al., *J. Med. Chem.* (1989) 32:548-555. Jimbo, et al., *Journal of Molecular Electronics* (1988) 4:111-118. Hanifeld, *Science* (1987) 236:450-453. Goundalkar, *Communications* (1984) 36:465-466. Cress, et al., *Amer. Biotec. Lab.* (February 1989) 16-20. Biosensors employing surfactant layer crystallization are described by Owen, *Ann. Clin. Biochem.* (1985) 22:555-564 and Thompson and Krull, *Trends in Anal. Chem.* (1984) 3(7):173-178. Bader, et al., *Advances in Polymer Sci.* (1985) 64:1-62 describe polymeric monolayers in liposomes as models for biomembranes.

Miller and Anderson, *Anal. Chim. Acta.*, (1989) 227:135-143, described a fiber-optic sensor based on a homogeneous fluorescence energy-transfer immunoassay and the chemical kinetics.

SUMMARY OF THE INVENTION

Biosensors are provided comprising an anisotropic polymeric lipid layer, where the polymer comprises a conjugated polyunsaturated extended chain and joined to the lipids are moieties, which are members of a specific binding pair. Specific binding to the moieties perturbs the anisotropic polymer lipid layer and changes the optical properties of the layer. By employing light, polarizers, waveplates and waveguides, singularly or in combination, optical signals may be obtained which reveal specific binding events involving the moieties attached to the lipid layer. The change in the optical characteristics of the light exiting from the film may be related to the number and/or manner of complexes which are formed. Devices are provided comprising a light source, means for orienting the light and directing the light to the lipid layer, the lipid layer, means for contacting the lipid layer with a sample, means for processing the light exiting from the lipid layer and means for detecting the characteristics of the light associated with the formation of specific binding complexes at the polymeric lipid layer surface.

DESCRIPTION OF THE SPECIFIC EMBODIMENTS

Biosensor devices and compositions associated with such devices are provided for the detection of analytes. Central to the device is the presence of a monolayer comprising polymerized lipids, polymerized through triple bonds to form an extended polyunsaturated chain which is anisotropic to li9ht and is capable of altering the characteristics of light passing through the layer. In addition, attached to the lipids are moieties which are members of a specific binding pair. By binding to the complementary member or a cross-reactive conjugate thereof, the optical properties of the film may be modulated in proportion to the number of specific binding pair complexes formed in the light path. By employing appropriate devices to define the polarization state, amplitude, and wavelength of the incident light, the number of binding complexes binding to the film can be related to the changes in the amplitude or polarization state of the exiting light.

The extended oriented polyunsaturated lipid layer may be prepared in a variety of ways, where the layer may be homogeneous or heterogeneous as to the number of unsaturated lipids which are involved in the polymer, the nature of the moieties bound to the lipids, and the like.

For the formation of large single crystal domain lipid films, a novel temperature gradient technique is employed (see U.S. Pat. No. 5,156,810 and application Ser. No. 453,784, filed Dec. 20, 1989, abandoned). Surfactant films may also be formed on the surface of an aqueous subphase by standard lipid monolayer technologies. A solution containing a monomeric surfactant composition, dissolved in an organic solvent, is applied to the subphase surface by a micropipet. Solvents may include hydrocarbons such as pentane, hexane, heptane, and decane. The hydrocarbons may be straight chain, branched, cyclic, or unsaturated. Solvents may include chlorocarbons such as mono-, di-, tri- or tetrachloroethane. The addition of more polar solvents such as alcohols, furans, ethers, esters, or the like may be added to enhance the solubility of the surfactant composition.

The subphase composition is one process variable which dictates the physical characteristics of the surfactant layer which is formed. The subphase can be composed of pure water, glycerol, polyethylene glycol, or other polar organic solvents miscible with water including DMF, DMSO, acetone, alcohols, ketones, furans, dioxane, ethanolamine, phenols, colloidal substances including dispersed carbon powder alone or in combination or the like. High boiling point solvents such as glycerol will reduce evaporation during heating, while low boiling point solvents will enhance the evaporation. Other organic solvents can be used to stabilize the surfactant film, particularly to favorably interact with the polar headgroups, linkers and ligands of the surfactant. The subphase can also contain organic or inorganic acids or bases which affect the surfactant film through ionic interactions, i.e., charge stabilization. The ionic components can include mono-and polyvalent ions and cations, and mono- and oligosaccharides.

Monomeric polymerizable surfactants are spread on the subphase at a concentration ranging from 0.01 to 50 milligrams/milliliter of spreading solvent. Typically 0.1 to 1.0 milligram/milliliter is most useful. Films are usually formed with a mixture of polymerizable surfactants including surfactant-linked ligands and filler surfactants which have no ligand attached. The polymerizable moiety of the filler surfactant is typically similar or identical to that of the ligand containing surfactant. The filler surfactant may have all the chemical characteristics of the ligand surfactant. It should have polar headgroups which are biologically inert and resilient to non-specific binding. As an example, the filler surfactant may have a hydroxyl, polyhydroxyl or polyethylene oxide headgroup which acts to prevent non-specific adherence of biological matter. The filler lipid could also contain a chromophore for enhancing the optic visualization of the film, and to enhance the photoelectrical injection of light. The mole percentage incorporation of the ligand-surfactant to the filler-surfactant plays a role in the support matrix. It is generally from 0.01 to 100% more usually from 0.1-10% and usually in the range of 1.0 to 5%. The composition of the polar headgroup of the filler-lipid can modulate the specific binding of biological material. Steric displacement can enhance protein binding, and steric hindrance could inhibit protein binding. The composition of the polar headgroup of the filler-lipid can thus provide a control mechanism for adjusting binding affinities and interactions, including responsiveness in an assay.

Film formation involves applying a subphase to a surface or well. A solution containing the monomeric surfactant is applied to a precleaned (aspirated) subphase surface until the surface is substantially saturated. The aqueous medium is preheated to melt and disperse the surfactant, usually to a temperature of not more than about 130° C., which results in evaporation of the solvent. The medium is then allowed to cool to below room temperature, usually to about 2° C. The rate of cooling, a key process variable for making highly crystalline films, is controlled by regulating the traverse rate of the subphase slide from the heating element to the cooling element. Typical traverse rates vary from 1 cm/second to 1 cm/minute. The formation of high quality films requires that the monomeric surfactant is highly crystalline at the gas/subphase interface. Crystalline films are often comprised of tightly packed single crystal domains. Large domains are desirable for manufacturing processes. Factors found to affect the domain size are crystallization temperature, spreading solvent composition, vibrations, convection currents in the subphase, superphase humidity (which affects the evaporation rate), subphase purity, and spreading solvent amount. The crystal growth can be initiated and controlled using a number of methods such as zone refinement, lateral film pressure, crystal re-annealing processes, site specific nucleation, the use of seed crystals, controlled atmospheric conditions, epitaxial crystallization, varying subphase composition, or the like. Large single crystals may be nucleated by initially crystallizing a surfactant film and then irradiating a narrow width of film using an intense UV laser source. When the subphase temperature is raised above the surfactant melting temperature, the non-polymerized regions of film will become fluid. When the subphase is cooled back below the surfactant melting transition, crystals of monomers nucleate from the crystalline polymer region.

The surfactant is then polymerized employing any convenient initiation system, e.g., ultra-violet light. Polymerization times are important for controlling the assay responsiveness of the films. Prolonged polymerization times (10 minutes) generally lead to non-responsive films. Polymerization times between 20 seconds to 5 minutes generally lead to more responsive films. Typically, 30 seconds to 2 minutes give the greatest response.

Other parameters, including the presence of inert gases or free radical initiators, can be used to control the polymerization rates and film responsiveness. Other initiation systems include combinations of light and light sensitive initiators, heat labile chemical initiators or the like. Such initiators are conventional and need not be described here. The activation is maintained until at least substantially complete polymerization is achieved. Polymerization may also be carried out by using electron beams, X-ray sources, synchotron radiation and the like. One method of polymerization involves site localized polymerization using focused laser light and an XY-controlled positioner, for the purpose of patterning circuits into the film [Ogawa, et al., Langmuir (1988) 4:195].

The film quality can be inspected optically using methods such as polarization birefringence, lateral diffusion techniques including lateral film pressure, or fluorescence measurements such as fluorescence recovery after photobleaching. Films are inspected for defects, crystal domain size and shape, and integrity. Defects may include point defects, edge defects, breakage, fractures. Crystal domain size and shape are characterized by various crystalline features such as dendritic patterns, large intact defect free domains, crystalline compactness and crystalline orientation. The film may be transferred to different substrates for production of the biosensor. Transfer is typically accomplished by slowly lowering a transfer substrate planar to the surfactant film at the air/subphase interface. Contact is made at one end of the subphase surface and then full transfer is accomplished by decreasing the contact angle to zero. Transfer may also be achieved by applying standard Langmuir-Blodgett methods [George L. Gaines Jr.: Insoluble Monolayers at Liquid Gas Interfaces, Interscience Publishers, I. Prigogine Editor, John Wiley and Sons (1964)].

The polymerizable surfactants have been extensively described in the literature as evidenced by the prior art described previously. The composition of the surfactant layer may be homogeneous where the surfactant is polymerizable and has a polar terminus, which may serve as a ligand for a complementary binding protein, or heterogeneous, where a mixture of surfactants are employed, some of which are polymerizable and others which are not polymerizable. The polymerizable and/or non-polymerizable surfactants may be the site for binding to a ligand.

The surfactant molecule may have a single lipid chain, e.g., a diynoic acid or a plurality of lipid chains, e.g., diester glycerides, preferably a single chain, and generally not more than two lipid chains.

Illustrative surfactants include ethanolamino-10,12-pentacosadiynamide, 6,8-hexadecadiynoic acid, 2-hydroxyethyl octadeca-8-10-diynoate, eicosa-12,14-diynyl-10, 12-phosphatidyl serine, pentaeicosa-10,12-diynoic acid, tricosa-10, 12-diynoic acid, acetylene compounds with multiple diyne groups and other polymer surfactants including single acyl chain polyerizable surfactants.

Various other surfactants may be present as diluents for the polymerizable surfactant. These surfactants may be naturally occurring, synthetic, or combinations thereof, and may be illustrated by laurate, stearate, arachidonate, cholesterol, bile acids, gangliosides, sphingomyelins, cerebrosides, or the like.

Various functional groups may be present in the film to provide for polymerization, which allow for Forster energy transfer. For the most part, the functional groups will comprise monoynes and diynes, although other polyunsaturated molecules may find use, such as activated monoynes, e.g., $\alpha$-ketomonoynes.

For the most part, the hydrophobic portion of the surfactant will have a chain of at least 6 aliphatic carbon atoms, usually a straight chain of at least 6 aliphatic carbon atoms, and generally not more than a total of about 100 carbon atoms, usually not more than about 34 carbon atoms. Preferably, the number of carbon atoms will vary from about 12 to 32, more usually 23 to 30, and more preferably 25 to 29 carbon atoms.

The lipid molecules will terminate in a hydrophilic moiety, cationic, anionic or neutral (nonionic) where the functionalities may include non-oxo carbonyl, e.g., carboxylic acids, esters and amides, oxo-carbonyl, such as aldehydes or ketones, oxy, such as ethers, polyethers, and hydroxyl, amino, such as primary, secondary, and tertiary amines and ammonium, phosphorus acids esters and amide, such as phosphate, phosphonate, and phosphonamide, sulfur functionalities, such as thiol, sulfonates, sulfate, and sulfonamides, and the like. Hydrophilic groups may include drugs or chromophores. Usually, the polymerizable functionality will be separated from the polar and non-polar termini by at least one carbon atom, generally from about 1 to 50 carbon atoms, more usually from about 1 to 8 carbon atoms. The polymerizable group is typically incorporated into the hydrophobic interior of the surfactant film. Examples of polymerized groups include polypyrrole, polyamines, polythiophene, poly(isothianaphthene) poly(alkylthiophene), polydiacetylene, polyacetylene or the like. Diacetylenic groups are typically incorporated in the hydrocarbon chain of the surfactant so that more than one group is present for polymerization. By having two or more polymerizable groups in the surfactant chain, a multiplicity of electrically conducting or optically active polymers may be obtained. This configuration leads to films of higher structural integrity and mechanical strength. The individual polymerizable groups can be spaced at regular intervals from 1–50 carbons apart, typically 2–10 carbon atoms apart. There can be as many of these groups in the chain as its length allows. Variations of the headgroup provide for improved film quality, such as stability of the film, surface charge, control of interhead-group hydrogen bonding, reduction of non-specific binding or fluid matrix effects, and ease of chemical modifications. The hydrocarbon tail of the surfactant may also terminate in a hydrophilic group so that the surfactant is bipolar. [Sher, *Justus Liebigs Ann. Chem.* (1954) 589:234; and Akimoto, et al. *Angew. Chem.* (1981) 20(1):91].

Depending upon the desired density of the ligand bound to the surfactant, the ligand size and the ligand's physical/chemical properties, the ligand may be present in from about 0.01 to 100 mol % of surfactant, more usually at least about 0.1 mol %, and preferably at least about 1 mol %, generally not more than about 10 mol %. The mol ratio will depend on the size and nature of the ligand, whether contiguous ligands are desired in the layer, and the like. The ligands may be joined by any convenient functionality, including esters, e.g., carboxylate and phosphate, ethers, either oxy or thio, amino, including ammonium, hydrazines, polyethylene oxides, amides, such as carboxamide, sulfonamide or phosphoramide, combinations thereof, or the like. Specific groups may involve saccharides, both mono- and polysaccharide, including aminosaccharides, carboxysaccharides, reduced saccharides, or the like. Specific groups include zwitterions, e.g., betaine, peptides, sugars, such as glucose, glucuronic acid, $\beta$-galactosamine, sialic acid, etc., phosphatidyl esters, such as phosphatidyl glycerol serine, inositol, etc.

The ligand can be any molecule, usually a small molecule, containing a reactive group. Typical ligands could be biotin, drugs such as alkaloids, chromophores, antigens, chelating compounds, crown ethers, molecular recognition complexes, polysaccharides, polypeptides, polynucleotides, ionic groups, polymerizable groups, fluorescence quenching groups, linker groups, electron donor or acceptor groups, hydrophobic groups or hydrophilic groups. The ligand may also serve as a site which can be further chemically modified to bring about new physical features or film characteristics.

The ligand can also be a photoactivateable or photocleavable group, in which case the possibility of biosensors for panel testing becomes very attractive. Using photoactivation or photocleavage and masking, one can selectively bind different receptors, antibodies, drugs or the like to the same biosensor, presenting tremendous advantages for panel testing or screening. Some of the advantages would be ease of screening, by simultaneously testing without extra steps, and cost. These panels could be used in research or in industry, for receptor testing, monoclonal antibody screening, infectious disease testing, therapeutic drug discovery in diagnostics for cancer screening, testing of drugs of abuse or therapeutic drugs, urinary tract infections, and sexually transmitted disease testing. The biosensor can also be used for environmental testing, in the food industry, and the like. A reusable biosensor panel could be incorporated into a flow cytometry instrument or other such instruments.

The articles of this invention can be prepared, for the most part, using conventional techniques employing particular conditions to achieve the desired layers. For the most part, Langmuir-Blodgett techniques will be employed as described in the references cited previously. In employing the subject methods, attention should be given to the experimental section for guidance as to the particular range that should be used with any particular parameter for the desired result.

A large number of parameters are available which can be used to influence the nature of the product. These parameters include the buffer, including pH, ionic strength, cations employed, e.g., mono- or polyvalent, composition of the surfactant, both as to the polymerizable surfactant and the nonpolymerizable surfactant, including such considerations as chain length, the status of the polymerizable functionality, the nature of the polymerizable functionality, and the nature of the polar head group; the manner in which the surfactant layer is formed, including concentration of surfactant and solvent, the nature of the solvent, the spreading method, the amount of surfactant employed, subphase composition, superphase composition, all of which will affect the formation of mono- or multilamellar layers; and physical parameters, such as film tension, crystallization time, temperature, humidity, traverse rates, E (electric) field and M (magnetic) field.

The ligands which are covalently bonded to the surfactant will normally be a member of a specific binding pair. Thus, the ligands may be varied widely, usually being molecules of less than about 2 kDal, more usually less than about 1 kDal. For the most part, the ligands will be considered to be haptenic, which may include small organic molecules, including oligopeptides, oligonucleotides, saccharides or oligosaccharides, or the like. However, in some situations, the ligand bound to the surfactant may be a macromolecule, usually not exceeding about 500 kDal, more usually not exceeding about 200 kDal. Thus, proteins, nucleic acids, or other polymeric or nonpolymeric compounds of high molecular weight may also be employed. There is also the possibility to use crown ethers which will bind to particular ions. The particular manner in which one or more surfactants may be bound to the ligand is not critical to this invention and will depend, for the most part, on convenience, ease of synthesis, stability, available functional groups, and the like. Synthetic macrocyclic complexes may be incorporated into the surfactant layer for the purpose of molecular recognition of various natural and non-natural compounds.

The ligand may be a molecule which can provide for covalent binding to another molecule. Carboxy groups may be activated with carbodiimide to react with alcohols, phenols and amines. Hydrazines may react with carboxylic acids, ketones and aldehydes, particularly under reducing conditions. Thiols can react with activated olefins, such as maleimide, acrylates, etc. or activated halides, e.g., iodoacetyl, and the like. For non-covalent or covalent binding, some enzyme substrates, inhibitors or suicide inhibitors may be employed with the complementary enzyme.

In many cases, particular ligands will be used for a variety of purposes. For example, biotin may be used to bind to avidin or streptavidin, where the complementary member may then be used to link a wide variety of other molecules. Various lectins may be employed to bind a variety of sugars which may be attached to molecules of interest. Specific ligands may be employed which bind to complementary receptors, such as surface membrane receptors, soluble receptors, or the like.

Of particular interest is the binding of receptor, either directly or indirectly, to the surfactant. Direct binding will usually be covalent, while indirect binding will usually be non-covalent, such as non-specific or specific adsorption. Receptors of particular interest will be antibodies, which include IgA., IgD, IgE, IgG and IgM, which may be monoclonal or polyclonal. The antibodies could be intact, their sulfhydryl bridges totally or partially cleaved, fragmented to $F(ab')_2$ or $Fab'$, or the like. The intact and totally cleaved antibodies could be used to make a recombinant protein A-antibody hybrid, to be incorporated into the assay. Coupling through the antibody's oligosaccharide moiety to hydrazines can be achieved with the intact, partially and totally cleaved antibody. Maleimide linkages could be used for the intact, partially and totally cleaved antibodies, and the $F(ab')_2$ fragment, while the Fab fragment could be incorporated in an antibody hybrid. Other examples for antibody coupling to polymer films will include the use of recombinant hybrid linker proteins and recombinant antibody molecules. The antibodies may be functionalized at the Fc portion to ensure the availability of the binding sites for further binding. Other receptors include naturally occurring receptors, such as viral receptors, surface membrane protein receptors, blood protein receptors, etc.

The oriented monomer films can be formed at gas-liquid interfaces and then transferred to scatter-free non-birefringent, transparent substrates, conveniently glass substrates. Transfer can be readily achieved by using conventional Langmuir-Blodgett conditions. The thickness of the substrate supporting the lipid layer will generally be from about 5 mil and not more than about 100 mil, preferably not more than about 50 mil. The significance is that the thickness does not interfere with the passage of light through the substrate. The substrate may be used in an evanescent wave mode. The substrate also provides the desired structural support. The surface of the substrate which serves to receive the polymer-surfactant layer and will be in contact with the surfactant layer should be clean and free of dirt and dust to minimize imperfections in the formation of the layer. For transferring polymerized surfactant films to the substrate by abutting the hydrophobic surface of the film to the substrate requires that the substrate be made hydrophobic. One process for making glass hydrophobic involves alkylation. An example of alkylation involves the use of a 5% solution of an alkylating agent in hexane. The agent can be a carbon chain with 1-50 carbons, usually 1-18, containing a methylalkylhalide silane group. For example, dimethyloctadecylchlorosilane may be used. After dipping and air drying, the glass is washed several times in chloroform, air dried, rinsed in high purity water for several minutes, and then air-dried again. The washing steps may be repeated several times. Unsaturated hydrocarbons may be used for surface alkylation to provide for a fluid hydrophobic layer. Cis-alkenes are conveniently employed. Transferring the polymerized film to a fluid hydrophobic layer provides for additional degrees of freedom in the polymerized layer. Binding events to the polymer layer can more readily distort the polymer layer providing for larger assay responses.

The monolayer polymerized films are particularly useful for analytical measurements due to the ease of attaching ligands and receptors to the films and the films' distinctive optical properties. The films are monomolecular, about 40 Å thick, so that surface binding events directly affect the intrinsic optical properties of the entire film. The arrangement of chemical bonds in the film results in a strongly absorbing, oriented chromophore so that the films are visibly colored and anisotropic, even though they are only one molecular layer thick.

For polydiacetylene monolayers, visible light passing through the film is strongly absorbed along the polymer axis, while negligible absorption occurs perpendicular to the polymer axis. The differential light absorption along the two optical axes is called linear dichroism. Light polarized along the strongly absorbing axis is also shifted in phase relative to light polarized along the other optical axis. This phase shift is called linear birefringence. The film response to polarized light also indicates the presence of circular dichroism and/or circular birefringence. Depending on detection methods, the light which is used may vary from UV to infrared usually being between about 200 and 1000 nm.

In general, a binding event can alter the linear dichroism, linear birefringence, circular dichroism, and circular birefringence of the film (either singularly or in combination). These changes can be measured using an instrument with a light source, a polarizer, wave plates, and an analyzer. These elements are employed to control the characteristics of the light entering the film and to select for measurement specific orientations and amplitude of the light exiting from the film. Usually, it will be desirable to split the light path, by any convenient means, so that light may pass through the sample and through a control or standard for comparison, so as to minimize the observed changes in the signal as a result of fluctuations in ambient conditions, assay matrix effects, light source, the light detecting system, and the like. In addition, a chopper may be employed to provide for a pulsed signal, which can be detected as an AC signal to increase the signal to noise ratio.

Polarized visible light (400–700 nm) may be employed which is incident on the polymer film with the absorbing axis at 45° to the polarization plane. The incident light is resolved into two polarized components, each of whose polarization planes contain one of the film's optical axes. The exiting light has a horizontal component which passes an analyzing polarizer and creates a signal in a photomultiplier tube.

Consider a beam of vertically polarized light entering the crystalline film and split into two components ($V_1$ and $V_2$) whose vibration planes are parallel to the optical axes of the crystal, $F_1$ and $F_2$, respectively. The crystal absorbs only visible light polarized along the $F_1$ axis and entirely passes light of the same wavelength polarized along the $F_2$ axis. Emerging from the crystal, light components along $F_1$ and $F_2$ recombine, and since the component along $F_1$ is partially absorbed by the layer, the polarization plane of the transmitted light (W) is rotated with respect to the polarization plane of the entering light (V). The analyzer passes only the horizontal component of W ($W_h$) whose intensity is measured by a photomultiplier.

The index of refraction, $\eta$, of the material has a real and imaginary component. The real part will measure the phase change and the imaginary part measure the amplitude change of the light as it passes through the material. With the anisotropic lipid layer, each component of $\eta$ will generally be a tensor. The subject layer is viewed as an anisotropic material having only two-dimensional order and thus, each component of $\eta$ can be described with only two numbers when limited to linearly polarized light. For the absorptive component of the index of refraction, these are $E_x$ and $E_y$. Since absorption is assumed to occur on only one axis, $E_y=0$. With light oriented at an angle $\alpha$ to the x direction of the film, absorption along y is zero and absorption along x reduces the x component of the incident beam, resulting in a transmitted beam of angle $\beta$. Thus, the change in angle can be related to the presence of specific binding pair complexes at the layer surface. Interaction of optical components with the film may be expressed mathematically utilizing Jone's calculus [Jones, C. R., J. Opt. Soc. Amer. 46(2), 126 (1956)].

The interaction of the subject films with circular polarized light is analogous to that of linearly polarized light. The subject films have shown a differential absorption of right and left circular polarized light. This measurement is sensitive to molecular conformational changes in the film. An instrument to measure this would use a Pockels cell to modulate visible collimated polarized light between linear and left circular, and linear and right circular polarization states. Using a lock-in amplification technique, the differential absorption of right and left circular polarized light would be obtained.

In carrying out the subject assay, a film on a substrate is employed, which film may be reusable or form a chip which may be discarded. The film may have different regions having different numbers of specific binding pairs, so that a number of assays may be carried out for different ligands. The lipid layer may just be contacted with a buffer solution as repeats, controls, or the like. The lipid layer will then be contacted with the sample, where the sample may or may not have been subject to prior treatment, such as removal of cells, filtration, dilution, concentration, detergent disruption to release antigen, centrifugation, or the like.

After sufficient time for complex formation, the incubation may be terminated by removal of the sample solution and the lipid layer measured or the lipid layer may be measured with the sample solution present. Usually, the sample solution will be removed and the layer dried by air, heat, or conveniently with a gas stream. By having a control region contiguous to the assay region, the two regions will be affected substantially the same, so that absolute dryness is not required. The sample and control regions may then be measured.

The various steps and reagents may be maintained at ambient conditions, although controlled temperatures in the range of about 20–40° C. may be employed. Washing may be employed, prior to and subsequent to incubation with the sample, the prior washing to block spots where non-specific binding may occur, by having protein in the wash, usually about 0.1-2 wt. % and/or detergent in about 0.01-2 wt. %. The subsequent washing will serve to remove non-specifically bound components from the sample. In some instances a reading may be taken in the presence of the wash solution.

Figure 1:
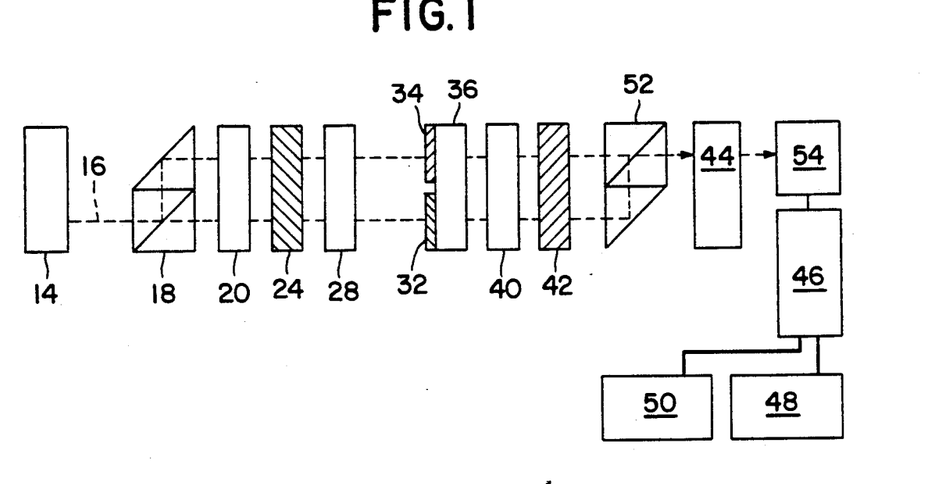
FIG. 1 is a diagrammatic view of an LCDB instrument according to this invention.

An apparatus which is useful in measuring analytes is depicted in FIG. 1. The instrument is used for measuring LCDB spectral changes upon an analyte binding event. A collimated point light source 14 is employed, where the collimated light 16 enters a beam splitter 18, which splits the beam into a dual light beam path. The dual light beam enters a motorized chopper 20 to modulate the light into specific pulse frequencies. The chopped dual beam light is passed through a polarizer 24 and then a wave plate 28, prior to the light interacting with the film and sample. The polarizer provides for the orientation of the light in a specific orientation, while the wave plate can be used to affect the phase of the light. The sample includes an analyte detection film 32 and a reference film 34. The films are supported on a transparent film substrate 36. After the dual beam light has passed through the sample and reference, it is passed through a wave plate 40, a polarizing analyzer 42, an interferometer 52, a monochrometer 44, and then to a photomultiplier 54. The analyzer is oriented close to 90° to the polarizer. The signals generated by the photomultiplier are amplified by the preamplifier 46 and then separated by lock-in amplifier 48 for sample beam and lock-in amplifier 50 for reference beam. Differential absorption of the light from the sample results in a spectral change. The use of interferometry (*Interferometry*, 2nd ed. *Cambridge Studies in Modern Optics*:1, Editors, P. L. Knight and S. D. Smith; FRS, by W. H. Steel, Cambridge University Press, 1967) in combination with the LCDB measurement provides for an efficient means of signal amplification. Interferometry is conveniently employed in the LCDB apparatus in a way which recombines the dual light beams which have passed through the test and control films. Recombination of the light beams results in an interference pattern because the differential light phase shift in the test sample compared with the control sample. The resulting phase shift is measured by nodes or amplitudes in the interference pattern. Changes in the spatially distinct interference pattern are directly monitored employing a slit between the interferometer and the monochrometer in the instrument. Interferometric methods have been utilized for measuring ultra-thin film thicknesses and are standard methods used by microscope manufacturers.

A large number of coupling pairs may be employed, where the binding may be covalent or noncovalent. Various proteins which bind specifically to a complementary ligand may be employed, such as enzymes, lectins, toxins, soluble receptors, antibodies, and the like. Illustrative proteins include DHFR, streptavidin, avidin, cholera toxin, lectins, the c-H-ras oncogene product, and nucleases. For linkages with oligosaccharides, hydrazine may used, by itself or bound to a polymer, e.g., poly(acrylhydrazide). Alternatively, biotin, nucleotides, or other molecular recognition analogs, or the like may be used. Nucleic acids, such as ssDNA or RNA may be employed. Maleimide linkages may be employed for linking to a thiol containing molecule, which may be biotin, avidin, any ligand or binding protein, sulfhydryl containing polymer, a nucleic acid, or molecular recognition analogs. For example, an intact antibody, with a functional oligosaccharide moiety, may be cleaved with periodic acid, and the resulting aldehyde reacted with the hydrazine under reductive conditions to form a stable carbon-nitrogen bond. For providing sulfhydryl groups to react with a maleimide, the antibody may be reduced at the hinge region, partially cleaved at the hinge region, or proteolytically cleaved near the hinge region for forming a thio ether with the activated olefin. In each case, care will be taken in selecting the method of linkage to ensure that the desired sites for binding to the complementary member of the specific binding pair are available for binding. Alternatively, sulfhydryl surfactants may be attached to sulfhydryl groups on the antibody molecules.

When the binding molecule should be maintained in an aqueous environment, the following procedure is found to be useful and may be treated as exemplary. An aqueous medium is formed, which is normally buffered at a pH in the range of about 4 to 9, preferably from about 5 to 9. The salt concentration will generally be in the range of about 10 mM to 1 molar. Illustrative buffers include phosphate, borate, barbitron, carbonate, Tris, MOPS, MES, etc. Illustrative buffer compositions include phosphate buffered saline; 138 mM NaCl, 50 mM potassium phosphate, pH 7.2; 200 mM sodium borate, pH 8.2, etc. Use of polyvalent ions is often desirable. The concentration of the multivalent cations will depend to some degree upon the nature of the cation, generally ranging from about 0.1 to 200 mM, more usually from about 10 to 100 mM and will be included in the determination of total salt concentration. The addition of detergents is often critical to reduce non-specific binding of the reagent to be coupled to the film particularly when the reagent is a protein. The amount of the detergent will depend on the nature of the protein, generally ranging from 0.001% to 10%, more from about 0.01% to 2%. Where non-specific adsorption of the binding member of the film is desirable, detergent may be left out. After submersing the polymer surface in an aqueous buffer containing from about 10–140 mM NaCl, 4–40 mM tris pH 6.5–7.5, as well as any additional appropriate coupling reagents and receptors, the reaction mixture is allowed to stand for sufficient time for completion of reaction, followed by washing. After activation with the complementary pair member, the biosensor will normally be covered for storage. The cover will be removable and will be removed prior to use. Various plastics may be used to seal the biosensor in a protective environment.

For carrying out an assay, the sample may be introduced onto the biosensor surface by direct injection into a reservoir buffer covering the sensor surface, by capillary action through a shallow flow cell covering the sensor, by fluid pumping through a flow cell, by gas phase adsorption and diffusion onto a wetted surface covering the sensor surface, or the like. For detecting extremely low concentrations of analyte, for example, less than about 10–12M, the flow cell method is preferred, since it allows a large volume of sample to pass over the sensor surface so as to concentrate the specific binding member on the surface. At higher concentrations, the reservoir sensor configuration is useful, because the diffusion rate becomes less of a factor.

On line monitoring of various biological processes, in vitro events and commercial processes is accomplished by placing a flow cell apparatus over the sensor surface. As the fluid is passed over the sensor surface, the analyte from solution binds to specific receptors on the sensor. Methods for signal generation will include direct, sandwich, and competitive antibody/antigen binding. Signals will be generated, for example, from antigen binding to biosensors, where the antibodies have been immobilized on the biosensor surface such that their antigen-binding sites are free for binding. Competition binding assays are used for small, usually monovalent analytes including proteins, peptide, oligosaccharides, oligonucleotides, drugs, and other small ligands. Competition assays may involve the use of mono- or multivalent ligands for signal amplification.

Depending upon the particular combination which is bound to the surface, a wide variety of different physical events may result, which allow for detection of a signal. The signal will result from perturbation of the polymerized surfactant layer resulting in a change in electrical, optical or structural properties of the polymerized surfactant layer. Where the analyte is small or structurally incapable of affecting the film, and its binding to an analyte binding molecule may have a small effect on the polymer layer, with little or no perturbation so as to prevent accurate detection, various methods may be used for signal enhancement.

Signal enhancement may be achieved by having a competition assay between the small ligand and ligand conjugate, where the conjugate may be bound to a particle, polymer, or other molecule which provides for enhanced perturbation of the film.

Different types of assays can be designed. In the case of DNA assays, single-stranded DNA is immobilized in the film using one or two points of attachment. The attachment may be covalent or noncovalent, e.g., biotin, avidin, hybridization, etc. When the sample containing a complementary strand of DNA is added, DNA duplexing leads to signal generation. In the case of a viral assay, virus capsid or envelope may bind directly to immobilized antibody or to specific viral receptors coupled to the film. Macromolecules will be assayed in a similar fashion to the viral assay. For serology, the same principle applies, but antigen is immobilized, and antibody is measured. Alpha-galactose-1,4-beta-galactose immobilized in the polymer film can bind to receptors of P. Fimbriea bacteria.

Neuraminidase inhibitors which bind to Influenza neuraminidase and sialic acid moieties which bind to Influenza hemagglutinin can be used for direct viral binding to the polymer film. Additional unoccupied sites remaining on the virus can serve as attachment sites for additional labels to provide a signal to the film that the virus is bound. Competition assays may be used for small molecules, in a displacement mode, where the competition occurs directly on the surface of the film, or in a more direct fashion, where a polyvalent cross-reacting moiety and the competitor analyte are added simultaneously to the biosensor. Various systems may be employed for detecting a variety of analytes. For example, with an antigen attached to the polymer, one may provide for a competition assay between the antigen on the polymer and the analyte antigen for a receptor, e.g., an antibody. The polymer may have coupled to it various effector molecules, such as chromophores for fluorescence energy transfer between the film and a fluorescence quenching molecule attached to the polymer-antigen complex. Alternatively, polyethylene glycol packing around the analyte molecule bound to the film may be employed, where analyte binding will displace the glycol to cause perturbation of the film. This assay avoids the need for competition. By having poly-ethylene glycol chains as a polar terminus of the surfactant, these molecules may align to form an ordered array.

Binding of the analyte may perturb the orderly packing leading to a structural change in the polymer layer. With polyvalent antigens cocking may be achieved, where cocking the binding of the polyvalent antigen results in bending of the film with a change in conformation of the polymer. The multivalent antigens may be prepared by chemically cross-linking antigens to beads, polymerized liposomes, macromolecular assemblies, water soluble polymers, such as polyacrylate sugars, chemically cross-linked molecules, chemically synthesized polyvalent molecules, or the like. Alternatively, drag/flow particles may be involved, where the particles compete with the analyte for binding to the surface. By having a flow of liquid past the particles, the polymer organization may be modified, with a change in signal. Another technique may involve quencher releasing complexes, such as microsponges, polymerized liposomes, macromolecular complexes, or self-quenching polymers. The presence of the quencher interacting with the surfactant polymer will provide for a change in the signal. Chromophores able to affect the optical properties of the polydiacetylene layer may be delivered to the layer in a variety of other ways. For example, the chromophore may be attached to a secondary antibody which sandwiches to an antibody bound to the analyte bound to the film. The chromophore may be a fluorescence quenching molecule which absorbs excited state energy from the polydiacetylene layer. Malachite green or other blue dyes absorbing in the range of 540 nm to 640 nm may be conveniently used. Standard coupling methods may be employed for attachment of the dye to the antibody.

Alternatively, chromophore molecules may be delivered to the film using an enzyme for amplification where the enzyme is covalently coupled to a secondary antibody molecule. Specifically, alkaline phosphatase is very effective for generating a blue dye precipitate which directly attaches to the polydiacetylene film. Both the LCDB spectra and fluorescence emission spectra are dramatically affected by the blue dye precipitate. The blue dye enzyme product crystallizes on the ordered organic polydiacetylene film resulting in two new peaks in the LCDB spectrum at approximately 610 nm and 675 nm, respectively. In the absence of the polydiacetylene layer, the enzyme product shows a distinct absorbance spectra, but no LCDB spectral peaks.

The blue dye alkaline phosphatase product also serves as a highly efficient fluorescence quencher. Blue dye, undetectable by eye or by absorbance spectrometers, is clearly detectable by quenching of fluorescence of the polydiacetylene layer. The high efficiency of fluorescence quenching may be due to the conjugated delocalized energy state of the polydiacetylene film.

Various tension devices may be employed, based on the use of actin and myosin. Thus, tension filaments or traversing actin filaments may be employed, with a resulting change in the conformation of the surfactant polymer.

Antiidiotypes may be employed as divalent and cocking probes, where antibodies may be bound to the surfactant polymer and binding of the ligand to the antibody would inhibit the binding of the antiidiotype. The polyvalence of the antiidiotype would result in crosslinking of the antibody bound to the surfactant and modification of the conformation of the polymer.

Divalent linker molecules with natural ligands attached at the end of a linker moiety can be used to prestrain the receptor/organic optical layer. Divalent binding results in a sterically strained surface if the linker between the ligands is somewhat inflexible, e.g., cyclic molecules, particularly aromatic linkers. Divalent molecules may be used in competitive analyte assays where the monovalent analyte of interest is eluted onto a prestrained surface. As the divalent moiety is displaced by the monovalent analyte, strain is released and the optical properties of the film change measurably.

Figure 2:
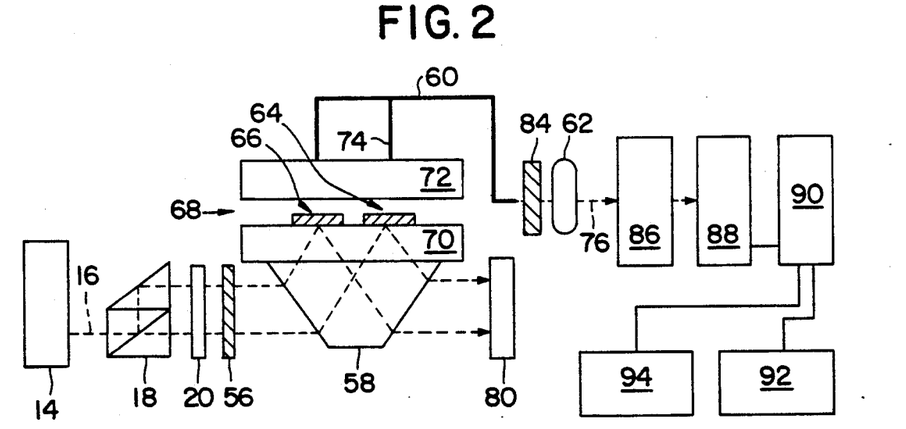
FIG. 2 is a diagrammatic view of a portion of an alternative embodiment.

Instead of passing light through the polymeric layer, evanescent fluorescent light may be employed, where the exciting light is shone at a shallow angle to the polyunsaturated film layer on the opposite side of the substrate, so that the exciting light wave is used to stimulate the layer. Fluorescence emission can be measured at a number of convenient angles. The measurement geometry is dependent upon a practical instrumentation and biosensor configuration. An instrument for measuring differential evanescent fluorescence is depicted in FIG. 2. Fluorescence utilizes a collimated point light source 14 to generate collimated light 16. The light is passed through a beam splitter 18, to create a dual beam for differentially measuring a sample and a reference film. The light is passed through a chopper 20 to generate pulses. The pulses will be used for frequency modulation and noise reduction. The dual beam light is passed through polarizer 56 to provide for linearly polarized light and then into a prism 58, coupled to a transparent substrate 70 where the light interacts with an analyte film 64, and reference film 66. The sample is added through the flow cell 68, formed between the substrate 70 and top 72. The light not absorbed by the sample is collected by the beam trap 80. Fluorescent light emitted from the sample and reference films is collected by a bifracted fiber optic cable 60, through fiber optic collection lens 74 directly over the analyte and reference films. Fluorescent light is passed through a polarized analyzer 84 to reduce scattered light and improve the signal to noise and then focused through the focusing lens 62 and the beam 76 directed into a monochrometer 86 and then a photomultiplier 88. The signals are amplified by the preamplifier 90, and then differentiated by a lock-in amplifier 92, for sample beam, and a lock-in amplifier 94, for reference beam.

Thus, by measuring the optical characteristics of the emitted light one may determine the degree of specific binding pair complex formation, while minimizing the presence of light from the light source entering the detector. Rather than observing the change in the optical characteristics of light passing through the polymeric lipid layer, one may provide instead for fluorescence from the polymeric lipid layer and measure the optical characteristics of the fluorescent light as it relates to the conformation of the polymer due to specific binding pair complex formation.

Infrared spectroscopy (IR) is of particular interest for analyzing conformational changes in the polymer film. IR has been used by others to study the solid state polymerization of heptadecadiyne-2,4-acid (Banerjie, A. and Lando, J. B.: *Polym. Prepr., Am. Chem. Soc., Div. Polym. Chem.,* 1978 Vol.: 19 no:2 pp.:170–5). IR bands of interest include the C≡C stretch (butatriene) and interactions at $V_1 = 2080$ cm$^{-1}$, and $V_2 = 1650$ cm$^{-1}$, and $V_3 = 860$ cm$^{-1}$. Additional stretching modes of interest include the acetylenic stretching mode, particularly the symmetric polymer stretch at $V_4 = 2100$ cm$^{-1}$. CH$_2$ out of plane deformation for CH$_2$ groups in the immediate vicinity of the depolarized $\eta$ electrons in the polymer are at $V_5 = 836$ cm$^{-1}$.

Since the vibrational states of the polymer are a direct measure of conformational change, and since multiple regions of the spectra can be affected by analyte binding, IR serves as a useful detection method for the polymerized lipid films described.

The following examples are offered by way of illustration and not by way of limitation.

EXPERIMENTS

A biosensor device was prepared as follows.

For various experiments, surfactant-linked ligands were prepared using condensation reactions involving an activated carboxylic acid group and a nucleophilic amine or hydroxyl. 10, 12-pentacosadiynoic acid was activated with trimethylacetylchloride under anhydrous conditions to form the active asymmetric anhydride. The anhydride was treated with excess ethylene diamine or ethanolamine (in situ) to form ethylenediamino-10,12-pentacosadiynamide (EDA-PDA) or ethanolamine-10,12-pentacosadiynamide (EA-PDA), respectively. 1.5 mole equivalents of triethylamine were added as a catalytic base. Reactions were allowed to proceed for 3 hours at room temperature. EDA-PDA. or EA-PDA were chromatographically purified using a silica gel column and a chloroform/methanol gradient. EDA-PDA or EA-PDA were condensed with free carboxylic acid containing ligands (chemically activated as above) to form the ligand-linked polymerizable surfactants. Representative examples of ligand linked surfactants which were prepared by this method for the purpose of fabricating biosensors include: 2,4-dinitrophenyl-aminocaproyl-EDA-PDA; theophylline-8-butyroyl-EDA-PDA; a-galactose-1,4-b-galactose-diethyleneoxide-aminosuccinyl-EDA-PDA; biotin-aminocaproyl-EDA-PDA; N-demethylrifampicin-succinyl-EDA-PDA; and dATP-EDA-PDA.

2,4-dinitrophenyl-aminocaproyl-EDA-PDA was prepared for fabricating a biosensor specific for anti-dinitrophenyl antibodies. Theophylline-8-butyroyl-EDA-PDA was prepared for fabricating a biosensor specific for anti-theophylline antibodies and theophylline assays. Biotin-aminocaproyl-EDA-PDA was prepared for the purpose of fabricating biosensors which utilize streptavidin as a binding member for various assays. N-demethylrifampicin-succinyl-EDA-PDA was prepared for the purpose of fabricating biosensor to detect RNA polymerase. dATP-EDA-PDA was prepared for the purpose of fabricating biosensors to detect enzymes and other proteins which bind to dATP. a-galactose-1,4,-b-galactose-diethyleneoxide-aminosuccinyl-EDA-PDA was prepared for the purpose of fabricating biosensors to detect P. Fimbrial strains of E. coli.

Ethanolamino-10, 12-pentacosadiynamide (EA-PDA) was also prepared for the purpose of forming mixed polymerized films. Films were usually prepared with 95-99.5 mole % EA-PDA and 0.5-5 mole % of any ligand-linked surfactant.

An illustrative assay is exemplified by employing a sample glass slide with a 2.5 mol percent theophylline-containing film (97.5 mol percent EA-PDA). The slide is analyzed by recording the LCDB spectra using a single beam version of an instrument described in FIG. 1. Before a spectrum is run, the maximum LCDB spectral intensity (relative percent transmission) on the slide is found by rotating the sample slide with respect to the instrument's polarizers. At this maximum position, 10 spectra are run from 400 to 700 nm.

The sample slide is removed from the spectrometer and a solution of PBST (phosphate-buffered saline, 0.05% Tween 20) is added to the sample area being analyzed. After a 10 min. incubation at room temperature, the PBST is rinsed off thoroughly with deionized water, blown dry with nitrogen, and reinserted into the instrument. 10 spectra are then run. The spectra after PBST are compared with the spectra taken of the dry film to demonstrate the response of film to buffer. The PBST spectra are then used as the new "blank" to compare to the next set of spectrum taken after antibody addition.

The sample slide is removed from the spectrometer and a solution of monoclonal anti-theophylline (50 μg/ml) and PBST is added to the sample area being analyzed. After 10 min. incubation at room temperature, the anti-theophylline is rinsed off with PBST, thoroughly rinsed with deionized water, blown dry with nitrogen, and reinserted into the spectrometer. 10 spectra are then run again. The data from the spectra are all automatically transferred to a computer for data analysis and graphing.

The following Table indicates spectral intensity changes measured at 545 nm before antibody treatment (PBST treatment) and after antibody treatment (mouse anti-theophylline treatment).

TABLE

Intensity Spectral Changes Before and After Antibody Treatment

| PBST treatment | mouse anti-theophylline treatment |
|---|---|
| 1.46 | 1.26 |
| 1.45 | 1.26 |
| 1.44 | 1.28 |
| 1.45 | 1.27 |
| 1.45 | 1.29 |
| 1.46 | 1.27 |
| 1.46 | 1.28 |
| 1.45 | 1.28 |
| 1.46 | 1.28 |
| 1.47 | 1.28 |

The numbers are expressed in terms of the relative transmission units of the LCDB spectrum. The average and standard deviation of the PBST spectra at 545 nm are 1.46 and 0.0085 respectively. The average and standard deviation after treatment are 1.28 and 0.0097 respectively. The calculated signal to noise for the experiment is 20 at 545 nm.

For a demonstration of specific blocking, films containing 2.5 mole percent theophylline-PDA and 97.5 mole percent EA-PDA were transferred onto dimethyloctadecylsilane treated glass slides. The films were first examined under crossed polarizers to select single crystal patches 10 mm square in size and then the slides mounted to the center of a rotational stage. The orientations of the crystals were determined by rotating the films relative to the two crossed Glan-Thompson prism polarizers inside the LCDB instrument. Maximum transmission occurred at 557 nm of the LCDB spectral when the crystal axes were aligned 45° relative to both polarizers; when minimum transmission occurred, the crystal orientation was parallel to either polarized axis. In order to obtain maximum signal, all subsequent experiments were performed with the crystal axis aligned 45° relative to both polarizers.

For the antibody blocking experiment, three films were prepared and treated as follows. A linear dichroic spectrum of each film was first taken in the initial dry state. After incubating PBST buffer solution over each film for 10 min., samples were washed with 300 μl of deionized water and dryed with nitrogen gas, followed by taking three more spectra. One film was then incubated with 100 μl of 100 μg/ml mouse antitheophylline in PBST for 10 min. Another film was subjected to 100 μl of 100 μg/ml mouse anti-theophylline with 100 μM of preincubated theophylline for 10 min. The third film was incubated with 100 μl of 100 μg/ml mouse anti-theophylline with 10 μM of preincubated theophylline for the same amount of time. After the incubation, all three films were washed with 300 μl of PBST, followed by deionized water, and dried with nitrogen gas. LCDB spectra were then taken again for each film.

The spectra were then graphically analyzed. LCDB spectra were scanned between 530 and 580 nm and the spectral peak areas integrated over 530 to 580 nm for the PBST treated films. Spectral differences were recorded between 530 and 557 nm after treatment with antibody with and without theophylline present in the sample. These integrated differences before and after sample treatment were divided by the integrated peak between 530 and 580 nm before sample treatment for normalized differences. The results are expressed as normalized integrated differences in the following Table.

TABLE

| Normalized Integrated Spectral Differences | |
|---|---|
| Concentration of theophylline ($\mu$M) | Normalized integrated before & after mouse anti-theophylline treatment |
| 0 | 130 |
| 10 | 50 |
| 100 | 20 |

For demonstration of fluorescence quenching, adjacent films, containing 2.5 mole percent theophylline-PDA and 97.5 mole percent EA-PDA for the test film and the other containing pure EA-PDA for the control film, were transferred side-by-side on alkylated glass slides. Flow cells were constructed by laminating a silicon rubber well, preformed on a second slide, to the slide containing the films. The flow cell dimension was 2 cm$^2$ and 1 mm deep. The flow cell and films were configured so that the test and control films, each 1 cm square, were side-by-side in the fluid path. Two prisms were attached to the slide containing the films coupled with an index matching fluid (Resolve). The flow cell device was placed in a mechanical holder in an instrument described in FIG. 2. A 543 nm Helium neon laser beam was split with a beam splitter and used to evanescently excite the PDA containing films. Fluorescence spectra were measured between 550 and 700 nm. The spectra were recorded and analyzed with a computer. Initially, the flow cell was filled with PBST and allowed to incubate for 10 minutes. 800 $\mu$l of a 1 ng/ml solution of mouse anti-theophylline in PBST was then injected into the flow cell and the solution allowed to incubate for 10 minutes. The flow cell was then flushed with 2 ml of PBST and then with 800 $\mu$l of a 5 $\mu$g/ml solution containing a horse anti-mouse: alkaline phosphatase immunoconjugate in PBST. The conjugate was allowed to incubate for 10 minutes and then the flow cell was flushed clean with 2 ml of PBST. At this point the fluorescence emission of both the test and control films were measured in real time using the instrumentation system described in FIG. 1. 800 $\mu$l of a solution containing alkaline phosphatase substrate (Vector Laboratories, BLUE KIT III) was added to the flow cell and the fluorescence spectra measured. The difference in spectral changes between test and control films were recorded in real time (test divided by control). Average difference and standard deviation were computed before and after enzyme substrate addition. The Table below summarizes different spectral data before and after the substrate addition in a test divided by control mode.

TABLE

| Differential Spectra Before and After Substrate Addition | |
|---|---|
| Before substrate addition | after substrate |
| 0.661 | 0.607 |
| 0.656 | 0.604 |
| 0.653 | 0.602 |
| 0.644 | 0.600 |
| 0.642 | 0.591 |
| 0.641 | 0.588 |
| 0.644 | 0.585 |
| 0.647 | 0.584 |
| 0.649 | 0.585 |
| 0.648 | 0.590 |
| 0.645 | 0.598 |

TABLE-continued

| Differential Spectra Before and After Substrate Addition | |
|---|---|
| Before substrate addition | after substrate |
| 0.643 | 0.601 |
| 0.642 | 0.604 |
| 0.642 | 0.605 |
| 0.643 | 0.609 |
| 0.644 | 0.609 |
| 0.653 | 0.607 |
| 0.654 | 0.606 |
| 0.656 | 0.607 |
| 0.657 | 0.604 |
| 0.659 | 0.601 |
| 0.660 | 0.599 |
| 0.661 | 0.598 |
| 0.660 | 0.596 |
| 0.656 | 0.596 |
| 0.652 | 0.600 |
| 0.644 | 0.606 |
| 0.644 | 0.610 |
| 0.639 | 0.612 |
| 0.639 | 0.614 |
| 0.639 | 0.617 |
| 0.639 | 0.619 |
| 0.644 | 0.617 |
| 0.642 | 0.621 |
| 0.636 | 0.624 |
| 0.646 | 0.626 |
| 0.648 | 0.626 |
| 0.647 | 0.626 |
| 0.646 | 0.624 |
| 0.647 | 0.626 |
| 0.649 | 0.623 |
| 0.650 | 0.619 |

The average and standard deviation before substrate addition was 0.653 and 0.0092 respectively. The average and standard deviation after substrate addition was 0.608 and 0.0105 respectively. The calculated signal to noise for the experiment was 4.57.

It is evident from the above results, that the subject apparatus and methodology provide for a simple, sensitive method for detecting low concentrations of ligands and receptors. The equipment is simple and minimizes the introduction of errors and materials interfering with the detection. Small volumes of samples may be employed with high sensitivity and reproducibility.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for determining the presence of an analyte in a sample, employing a detection system comprising a polymerized polyunsaturated lipid oriented crystalline layer having extended conjugated aliphatic unsaturation and groups proximal to one surface of said layer, wherein said groups are one member of a specific binding pair and said analyte is a member of said specific binding pair, wherein said surface has a sample region and a control region, wherein a value is obtained for at least one of the intensity, orientation and amplitude of light emanating from said regions of said polyunsaturated lipid layer surface, said method comprising:

contacting said sample region of said lipid layer surface with said sample in a liquid assay medium, and contacting said control region of said lipid layer with said liquid assay medium, and contacting both said regions with any additional reagents required to change the optical characteristics of said layer in relation to the presence of said analyte;
substantially drying each of said regions;
irradiating said regions with collimated light;
determining a sample and control value of at least one of the intensity, orientation and amplitude of light emanating from said regions; and
comparing the difference in values from said sample region of said polyunsaturated lipid layer surface before said contacting and after said drying, with the difference in values from said control region of said polyunsaturated lipid layer surface before said contacting and after said drying, as a determination of the presence of said analyte in said sample.

2. A method according to claim 1, wherein said collimated light is polarized light.

3. A method according to claim 1, wherein said irradiating is with evanescent light and said light emanating from said layer is fluorescent light.

4. A method according to claim 1, wherein said additional reagents comprise a member of said specific binding pair conjugated to an enzyme.

5. A method according to claim 4, wherein said additional reagents further comprise an enzyme substrate which produces an insoluble product which changes the optical characteristics of said lipid layer.

* * * * *